United States Patent [19]

Zielke et al.

[11] 4,296,260

[45] Oct. 20, 1981

[54] PROCESS FOR THE PREPARATION OF PHLOROGLUCINOL

[75] Inventors: Rainer Zielke, Erlenbach; Helmut Maegerlein, Obernburg, both of Fed. Rep. of Germany

[73] Assignee: Akzona Incorporated, Asheville, N.C.

[21] Appl. No.: 64,691

[22] Filed: Aug. 8, 1979

[30] Foreign Application Priority Data

Sep. 18, 1978 [DE] Fed. Rep. of Germany ....... 2840597

[51] Int. Cl.$^3$ ....................... C07C 39/10; C07C 37/01
[52] U.S. Cl. ..................................... 568/763; 568/770
[58] Field of Search ................ 568/763, 770, 772, 774

[56] References Cited

U.S. PATENT DOCUMENTS

| | | | |
|---|---|---|---|
| 2,461,498 | 2/1949 | Krueger . | |
| 2,799,698 | 7/1957 | Taves | 568/771 |
| 3,028,410 | 4/1962 | Zimmer, Jr. et al. | 568/766 |
| 3,230,266 | 1/1966 | Baldonia et al. | 568/770 |
| 3,904,695 | 9/1975 | Hendrickx et al. | 568/770 |
| 3,959,388 | 5/1976 | de Haij et al. | 568/770 |
| 3,959,399 | 5/1976 | Bridwell . | |
| 4,093,667 | 6/1978 | Starks | 568/766 |

FOREIGN PATENT DOCUMENTS

| | | | |
|---|---|---|---|
| 102358 | 3/1899 | Fed. Rep. of Germany | 568/767 |
| 813709 | 9/1951 | Fed. Rep. of Germany | 568/767 |
| 1195327 | 3/1966 | Fed. Rep. of Germany | 568/767 |
| 1195327 | 3/1966 | Fed. Rep. of Germany | 568/767 |
| 2231005 | 1/1973 | Fed. Rep. of Germany | 568/770 |
| 2362694 | 6/1974 | Fed. Rep. of Germany . | |
| 2502420 | 9/1976 | Fed. Rep. of Germany | 568/767 |
| 2621431 | 11/1977 | Fed. Rep. of Germany , | |
| 1289647 | 2/1962 | France . | |
| 12239 | 4/1955 | German Democratic Rep. | 568/771 |
| 24998 | 3/1963 | German Democratic Rep. . | |
| 751598 | 6/1956 | United Kingdom | 568/768 |
| 1012782 | 12/1965 | United Kingdom | 568/767 |
| 1022733 | 3/1966 | United Kingdom | 568/767 |
| 1106088 | 3/1968 | United Kingdom | 568/767 |
| 1274551 | 5/1972 | United Kingdom | 568/767 |
| 1431501 | 4/1976 | United Kingdom | 568/770 |

OTHER PUBLICATIONS

Baeyer, "Ber." 18 3454 (1885).
Willstaetter, "Ber." 32. 1272 (1899).
Leuchs, "Ber." 41 3172 (1908).
Komminos, "Bull. Soc. Chem. Fr." 23, 449 (1918).
McKillop et al., "Synthetic Communications" 4 (1) 43,35 (1974).
Heertjes, "Recuell" 78, 452 (1959).
Weidel et al., "Monatsh." 21, 15 (1900).
Hepp, "Ann" 215, 348 (1932).
Organic Synthesis Coll. vol. I, 444 (1932).
Gill et al., "J. Chem. Soc., " 1753 (1949).
Kastens, "Ind. and Engin. Chem." 42, 402 (1950).
Desseigne "Mem. Poudres" 44, 325 (1962).
Flesch, "Monatsh" 18, 775 (1897).
Seidel et al., "Journ. praky. Chemie" 275 278 (1958).

Primary Examiner—Werren B. Lone
Attorney, Agent, or Firm—Francis W. Young; Robert F. Green

[57] ABSTRACT

A process for the preparation of phloroglucinol is disclosed. The process comprises reacting hexachlorobenzene with sodium propylate or sodium isopropylate, in a molar ratio of from about 1:3 to about 1:20, in an aprotic solvent, at a temperature from about 50 to about 250° C., to form trichlorophloroglucinol tripropylether, or trichlorophloroglucinol triisopropylether. The latter compounds are dechlorinated to form phloroglucinol tripropylether or phloroglucinol triisopropylether, with the use of metallic sodium, and subsequently hydrolyzed to form phloroglucinol.

8 Claims, No Drawings

PROCESS FOR THE PREPARATION OF PHLOROGLUCINOL

BACKGROUND OF THE INVENTION

This invention relates to a process for the preparation of phloroglucinol.

Several processes for making phloroglucinol are already known. In particular, the reduction of 1,3,5-trinitrobenzene to 1,3,5-triaminobenzene and its subsequent hydrolysis to form phloroglucinol is industrially important. According to older processes, the reduction step may be accomplished by utilizing tin in hydrochloric solution (Weidel and Pollak, Monatsh. 21, 15, (1900); Hepp. Ann. 215, 348; Organic Synthesis Coll. Vol. I, 444 (1932); U.S. Pat. No. 2,461,498), or with hydrogen and Raney nickel in an organic solvent, such as ethyl acetate (German Pat. No. 813,709; Gill et al., J. Chem. Soc. 1753 (1949); British Pat. No. 1,106,088). A reducing agent suitable for the large-scale industrial reduction of the trinitrobenzene is iron/hydrochloric acid (U.S. Pat. No. 2,614,126; Kastens, Ind. and Engin. Chem. 42, 402 (1950); British Pat. No. 1,022,733). Platinum, palladium and rhodium catalysts have also been proposed for the reduction of trinitrobenzene (French Pat. No. 1,289,647; Desseigne, Mem. Poudres 44, 325 (1962). In such a synthesis, instead of starting with 1,3,5-trinitrobenzene, one can also start with 2,4,6-trinitrobenzoic acid, which on a large scale is obtainable through the oxidation of trinitrotoluene with sodium dichromate in sulfuric acid (Kastens, l.c.), since the 2,4,6-triaminobenzoic acid formed in the reduction either decarboxylates immediately to triaminobenzene, or is converted to phloroglucinol during the subsequent hydrolysis (British Pat. Nos. 1,022,733; 1,106,088; 1,274,551). Furthermore, it is known to start with 5-nitro-1,3-diaminobenzene instead of trinitrobenzene (British Pat. No. 1,012,782. The hydrolysis of the triamine to phloroglucinol is customarily carried out in a mineral acid solution (Flesch, Monatsh. 18,755 (1897); German Pat. No. 102,358, or, according to a more recent process, in the presence of copper and/or its salts as catalysts (German Pat. No. 1,195,327).

According to a process likewise of interest from an industrial viewpoint, one may obtain phloroglucinol by oxidizing 1,3,5-triisopropyl benzene, separating the trihydroperoxide from the resulting mixture of mono-, di- and trihydroperoxides, and subjecting it subsequently to ketone splitting (British Pat. No. 751,598; German Pat. No. 12,239; Seidel et al., Journ. prakt. Chemie 275, 278 (1956). It is also possible to convert triisopropyl benzene directly to phloroglucinol triacetate through oxidation with oxygen in acetic anhydride, followed by hydrolysis with alcoholic sodium hydroxide to form phloroglucinol. One may also start with m-isopropyl resorcinol, which is esterified with acetic anhydride; the resulting m-isopropyl resorcinol diacetate is then oxidized to hydroperoxide and the latter is finally converted to phloroglucinol with acid (U.S. Pat. No. 3,028,410). Phloroglucinol may also be obtained, if resorcinol (Barth and Schreder, Ber. 12, 503, (1879), resorcinol substituted in 2-, 4-, 5-, 3,5- or 2,4-position by chlorine or bromine (German Pat. No. 2,231,005), or 1,3,5-benzene trisulfonic acid (U.S. Pat. No. 2,773,908) are melted with excess alkali hydroxide.

In addition to the listed benzene derivatives, mention has also been made of hexahydroxybenzene, picryl chloride, tetrachloro- and tetrabromobenzene, as well as tribromobenzene, as initial materials for phloroglucinol synthesis. Hexahydroxybenzene may be hydrated with platinum oxide in an aqueous medium (Kuhn et al., Ann. 565, 1 (1949), picryl chloride may be reduced with tin and hydrochloric acid, or electrolytically, and the 1,3,5-triaminobenzene, or 2,4,6-triamino-1-chlorobenzene obtained thereby may then be hydrolyzed (Heertjes, Recueil 78, 452 (1959).

The above-mentioned tetrahalobenzenes may be subjected to ammonolysis in the presence of a copper catalyst and the intermediary triamine may be hydrolyzed in the reaction mixture without a preceding separation (U.S. Pat. No. 3,230,266). Tribromobenzene may be converted to 1,3,5-trimethoxybenzene with sodium methanolate and catalytic quantities of copper iodide in methanol/dimethyl formamide as a solvent, and also may be subsequently subjected to hydrolysis (McKillop et al., Synthetic Communications 4 (1) 43,35 (1974).

Reference may also be made to the process of German Patent Disclosure No. 2,362,694, according to which 2,6-, 2,4-, 2,5-, or 3,5-dihalogen phenols dissolved in pseudo-cumene are heated in the presence of a strong alkali.

Furthermore, there is also a known phloroglucinol synthesis based on diethyl malonate. When subjected to treatment with metallic sodium, the malonic diethyl ester may condense with itself to form the trisodium salt of phloroglucinol dicarboxylic diethyl ester and this intermediate product may then be subjected to alkaline hydrolysis and decarboxylation (v. Baeyer, Ber. 18, 3454 (1885); Willstaetter, Ber. 32, 1272 (1899); Leuchs, Ber. 41, 3172 (1908); Komninos, Bull. Soc. Chem. Fr. 23, 449 (1918). Such a synthesis has been improved to the extent that the formation of the sodium malonic diethyl ester and the trisodium salt of phloroglucinol dicarboxylic diethyl ester may be performed in a single operation by means of boiling in an inert, high-boiling solvent, preferably dekalin (East German Pat. No. 24,998).

From the above-mentioned processes, apparently only the process based upon 2,4,5-trinitrobenzoic acid has been utilized commercially. However, such a process has several serious drawbacks. 2,4,5-trinitrobenzoic acid may be prepared by oxidizing trinitrotoluene, which is explosive, thus rendering such a process dangerous. In addition, the total yield, measured on the basis of 2,4,6-trinitrobenzene, of phloroglucinol produced via the intermediates of trinitrobenzene and triaminobenzene, is low. Such a process is also disadvantageous because the waste water formed during the oxidation and reduction is strongly acid and contains the heavy metals chromium and iron, and must therefore be treated.

Very recently, two additional technical synthesis of phloroglucinol have been discovered. According to the process disclosed in U.S. Pat. No. 4,123,461, benzenetricarboxylic acid-(1,3,5)-triamide is chlorinated in an aqueous mineral acid medium, the resulting benzenetricarboxylic acid-(1,3,5)-tri-N-chloramide, upon treatment with ammonium, is converted to 1,3,5-triureido benzene, and the latter compound subsequently hydrolyzed in a mineral acid solution. According to the process disclosed in U.S. Pat. No. 4,071,555, s-triacetyl benzene is converted into benzene-1,3,5-trisacetoxime, which is subjected to a Beckmann rearrangement, whereupon the resulting mixture and substances are subjected to acid hydrolysis. In both of the latter processes the initial materials are easily accessible, the yields are high, and pure products are obtained.

SUMMARY OF THE INVENTION

There has now been discovered an additional industrial-scale synthesis for phloroglucinol which commences with an easily accessible initial material, namely hexachlorobenzene.

There has thus been discovered a process for the preparation of phloroglucinol comprising reacting hexachlorobenzene with sodium propylate, in a molar ratio of about 1:3 to about 1:20, respectively, in an aprotic solvent, at a temperature from about 50° to about 250° C., to form trichlorophloroglucinol tripropylether, dechlorinating the trichlorophloroglucinol tripropylether with metallic sodium to form phloroglucinol tripropylether, and hydrolyzing the phloroglucinol tripropylether to form phloroglucinol.

Alternatively, the process comprises reacting hexachlorobenzene with sodium isopropylate, in a molar ratio of about 1:3 to about 1:20, respectively, in an aprotic solvent, at a temperature from about 50° to about 250° C., to form trichlorophloroglucinol triisopropylether, dechlorinating the trichlorophloroglucinol triisopropylether with metallic sodium to form phloroglucinol triisopropylether, and hydrolyzing the phloroglucinol triisopropylether to form phloroglucinol.

DETAILED DESCRIPTION OF THE PREFERRED EMBODIMENTS

Hexachlorobenzene is, of course, industrially available in large quantities, such as from waste product obtained from the chlorination of propylene. Because of its toxicity, hexachlorobenzene is a troublesome compound, the utilization and disposal of which has presented great difficulties. Small quantities of the compound can be used in the preparation of chloranil (by oxidation) and some quantities may be utilized to produce pentachlorophenol, to be utilized in wood preservatives. However, it appears that such an area of utility will soon no longer be available, for ecological reasons.

Thus, the largest part of the hexachlorobenzene produced cannot be utilized, nor can it be burned nor buried. Until now, the hexachlorobenzene had to be disposed of by chemical means and thus today there are firms which specialize in the disposal of hexachlorobenzene, at relatively high costs. It is therefore extremely advantageous that a sensible possibility for utilizing hexachlorobenzene is thus made available with the process of the present invention.

Instead of pure hexachlorobenzene, it is also possible to utilize the mixtures of chlorinated hydrocarbon wastes resulting from industrial processes. An example are the mixtures obtained in the chlorination of propylene, which consist of about 65% by weight hexachlorobenzene, about 25%, by weight, hexachlorobutadiene, and about 10%, by weight, hexachloroethane. Such by-products can easily be separated from the hexachlorobenzenes, as by extraction with methanol.

Reaction of the hexachlorobenzene with the alcoholate takes place at temperatures in a range from about 50° to about 250° C. Lower, or higher temperatures are also possible, but not advantageous for economic reasons. The preferred reaction temperature is between about 100° and about 200° C.

Sodium propylate, or sodium isopropylate, may be prepared from sodium and propyl alcohol, or isopropyl alcohol, in a customary manner. It is used in quantities of about 3 to about 20 mols per mol of hexachlorobenzene. In order to guarantee a complete conversion of the hexachlorobenzene, the quantity of sodium propylate or isopropylate should not be any less. Higher quantities of alcoholate should be avoided for economic reasons. Preferably, use is made of 5 to 6 times the molar quantity of sodium propylate, or sodium isopropylate.

Pursuant to the invention, aprotic solvents are used in the synthesis of the phloroglucinol ether. All usual aprotic solvents are suitable, such as the N-dialkylated amides of short-chain carboxylic acids, such as dimethyl formamide, diethyl formamide and dimethyl acetamide; dimethyl sulfone; tetramethyl sulfone; and dimethyl-tetramethylene sulfone. Preference is given to hexamethylphosphoric triamide, methylphosphonic tetramethyl diamide, dimethyl sulfoxide, N-methyl pyrrolidone, pyridine, or N,N,N',N'-tetramethyl ethylene diamine. The quantity of solvent is not critical. Preferably, the weight ratio of hexachlorobenzene to solvent is about 1:1 to about 1:50, in particular about 1:5 to about 1:10.

The hexachlorobenzene is reacted with the alcoholate in the manner customary for oxalkylation, as by heating the mixture of hexachlorobenzene, alcoholate and solvent until termination of the reaction, for example with reflux, whereupon the solvent is drawn off and the residue distilled after separation of the inorganic salts.

When the process conditions pursuant to the invention are maintained, oxalkylation surprisingly proceeds with high selectivity to form the desired tri-ether. This is surprising because, when sodium methylate is used, this nucleophilic substitution of the hexachlorobenzene proceeds preponderantly to form a mixture of the isomeric disubstitution products. One obtains thereby a mixture of 63–65 mol % tetrachlororesorcinol dimethylether, 23–26 mol % tetrachloropyrocatechol dimethylether, and 2 to 10 mol % tetrachlorohydroquinone dimethylether. In addition, trichlorophloroglucinol trimethylether is formed with a yield of only 4–7 mol % (G. G. Yakobson et al., Zh. Obshch. Khim. 35 (1), 137 (1965); C.A. 62, 13 073 (1965)). Similar results are also obtained, when sodium ethylate is used. Such reaction mixtures are of course not suitable for the preparation of phloroglucinol. Even when the higher-molecular, homologous alcoholates, such as sodium butylate, are used, oxalkylation proceed less selectively than in the process pursuant to the invention. In the process pursuant to the present invention, however, the nucleophilic substitution surprisingly proceeds preponderantly in the 1,3,5-position, to form trichlorophloroglucinol trialkylether, and with selectivities in a range from 85 to 95% and with yields in a range from 80 to 90% of theoretical.

The trichlorophloroglucinol tripropyl- and triisopropylethers obtained in the manner described above may be dechlorinated with metallic sodium in the manner customary for the dechlorination of aromatic halogen hydrocarbons. In keeping therewith, the trichlorophloroglucinol ether may be dissolved in a suitable solvent, as in an alcohol such as ethanol, propanol, or isopropanol, mixed with an excess of metallic sodium and heated until the sodium has been completely dissolved. The reaction mixture is then diluted with water and the dechlorinated product is extracted with a suitable solvent, such as ethyl ether, methylene chloride, chloroform, or hexane. When this extract is distilled, the phloroglucinol trialkylether is obtained in pure form. In this stage of the process, the yield is practically quantitative.

Hydrolysis of the phloroglucinol ether may be performed in the manner customary for this type of compound, as with hydrogen chloride or other mineral acids, like sulfuric acid or hydrogen bromide. For economic reasons, one typically uses hydrogen chloride. It is also possible to use mixtures of hydrogen halide and glacial acetic acid or acetic anhydride. Preferably, the hydrolysis is performed with concentrated hydrochloric acid and at room temperature, from about 15° to about 25° C. This stage of the reaction also proceeds practically quantitatively.

The process pursuant to the present invention is especially suited for the industrial-scale preparation of phloroglucinol. Aside from the high yield and the ease of execution, its special advantage is based on the fact that one can use a raw material that is essentially cost-free and additionally contribute to the protection of the environment.

Phloroglucinol is used as a developer in the diazotype process, as a cross-linking, vulcanizing, stabilizing or anticorrosion agent, as well as a coupling component in the preparation of numerous dyestuffs. In analysis it is used as a reagent for aldehydes, pentoses, lignin, galactoses and other substances. It is furthermore needed in the preparation of coumarins, flavonols and pharmaceuticals.

The process pursuant to the invention is explained in further detail in the following non-limiting examples.

A. Preparation of Trichlorophloroglucinol Ether

EXAMPLE 1

7.13 g (0.025 mol) hexachlorobenzene and 12.3 g (0.15 mol) sodium propylate were heated for 2 hours in 50 ml pyridine with reflux. The cooled reaction mixture was diluted with 200 ml of water and acidified to a pH of 5 with hydrochloric acid of 10% by weight. This was followed by two extractions, each with 100 ml of chloroform. The extraction agent was drawn off in a vacuum and the residue distilled at 2 to 3 mbar and an airbath temperature of 150° to 200° C., on the bulb tube. A total of 8.35 g (94% of theoretical) of the isomeric tripropoxytrichlorobenzenes was obtained. 85% of the mixture consisted of the desired trichlorophloroglucinol tripropylether. This corresponds to a yield of 80%, based on the hexachlorobenzene.

EXAMPLE 2

28.5 g (0.1 mol) hexachlorobenzene and 49.2 g (0.6 mol) sodium isopropylate were heated for 2 hours in 200 ml pyridine with reflux. The majority of the pyridine was then distilled off and the residue, while being cooled, mixed with 150 ml hydrochloric acid of 10% by weight. The organic phase was taken up in 100 ml carbon tetrachloride and dried with sodium sulfate. Distilling off of the solvent was followed by distilling on the bulb tube (2 mbar, airbath temperature 180°-200° C.).

33.5 g of distillate were obtained, which contained 90% of the desired trichlorophloroglucinol triisopropylether, corresponding to a yield of 84.4% of theoretical. 27.5 g of the pure product with a melting point of 55° C. were obtained by recrystallization from 50 ml methanol.

EXAMPLE 3

50 g of a mixture of chlorinated hydrocarbon wastes, consisting of 65% hexachlorobenzene, 25% hexachlorobutadiene and 10% hexachloroethane were mixed with 100 ml methanol and stirred for an hour at 20° C. 32 g of insoluble constituents were separated, which consisted of pure hexachlorobenzene. The residue (0.112 mol hexachlorobenzene) was dissolved in 400 ml dimethyl formamide and stirred overnight at 140° C. in the presence of 50 g (0.61 mol) sodium isopropylate. The solvent was distilled off, and the trichlorophloroglucinol triisopropylether remaining in the residue obtained in the manner described for Example 2. The yield was 35.8 g (87% of theoretical, based on the hexachlorobenzene content of the waste mixture).

B. Dechlorination of the Trichlorophloroglucinol Ether

EXAMPLE 4

3.55 g (0.01 mol) trichlorophloroglucinol triisopropylether in 100 ml isopropanol were mixed with 5 g sodium. Heating with reflux was continued until all sodium had been dissolved. This was followed by diluting with 100 ml water, neutralizing with hydrochloric acid of 15% by weight, taking up of the organic phase in ethyl ether, drawing off of the ethyl ether and distilling of the residue on a bulb tube (2-3 mbar, airbath temperature 130° to 150° C.). 2.47 g phloroglucinol triisopropylether were obtained, which corresponds to a yield of 98% of theoretical.

EXAMPLE 5

Trichlorophloroglucinol tripropylether was dechlorinated in the manner described for Example 4. 2.45 g phloroglucinol tripropylether were obtained, which corresponded to a yield of 97.2% of theoretical.

C. Ether Splitting of the Phloroglucinol Triethers

EXAMPLE 6

2.52 g (10 mmol) phloroglucinol triisopropylether and 150 ml concentrated hydrochloric acid were stirred overnight at room temperature. Traces of precipitated phloroglucide were removed by suction and the filtrate mixed with sodium carbonate until a pH value of 2-3 had been reached. This was followed by continuous extraction with ethyl ether and concentration of the ether extract. The residue consisting of phloroglucinol and some phloroglucide was recrystallized from water. The yield was 1.38 g, corresponding to 85.2% of theoretical (phloroglucinol dihydrate).

What is claimed is:

1. A process for the preparation of phloroglucinol comprising reacting hexachlorobenzene with sodium propylate in a molar ratio of hexachlorobenzene:sodium propylate of from about 1:3 to about 1:20, in an aprotic solvent, and at a temperature from about 50° to about 250° C. to form trichlorophloroglucinol tripropylether, dechlorinating the trichlorophloroglucinol tripropylether with metallic sodium to form phloroglucinol tripropylether, and hydrolyzing the phloroglucinol tripropylether to form phloroglucinol.

2. A process for the preparation of phloroglucinol comprising reacting hexachlorobenzene with sodium isopropylate in a molar ratio of hexachlorobenzene:sodium isopropylate of from about 1:3 to about 1:20, in an aprotic solvent, and at a temperature from about 50° to about 250° C. to form trichlorophloroglucinol triisopropylether, dechlorinating the trichlorophloroglucinol triisopropylether with metallic sodium to form phloroglucinol triisopropylether, and hydrolyzing the phloroglucinol triisopropylether to form phloroglucinol.

3. The process of claim 1 wherein the molar ratio of hexachlorobenzene:sodium propylate is from about 1:5 to about 1:6.

4. The process of claim 2 wherein the molar ratio of hexachlorobenzene:sodium isopropylate is from about 1:5 to about 1:6.

5. The process of claim 1, 2, 3, or 4 wherein the reaction temperature is from about 100° to about 200° C.

6. The process of claim 1, 2, 3, or 4 wherein the aprotic solvent is selected from the group consisting of hexamethylphosphoric triamide, methylphosphonic tetramethyl diamide, dimethyl sulfoxide, dimethyl formamide, N-methyl pyrrolidone, pyridine, or N,N,N',N'-tetramethyl ethylene diamine.

7. The process of claim 1, 2, 3, or 4 wherein the hydrolyzing step is performed with concentrated mineral acid.

8. The process of claim 6 wherein the hydrolyzing step is performed with concentrated mineral acid.

* * * * *